United States Patent [19]

Rasshofer et al.

[11] Patent Number: 4,472,568
[45] Date of Patent: Sep. 18, 1984

[54] PROCESS FOR THE PREPARATION OF POLYAMINES FROM N-MONOARYL-N',N'-DIALKYL UREA COMPOUNDS AND THEIR USE FOR THE SYNTHESIS OF POLYURETHANES

[75] Inventors: Werner Rasshofer, Cologne; Gerhard Grögler, Leverkusen, both of Fed. Rep. of Germany

[73] Assignee: Bayer Aktiengesellschaft, Leverkusen, Fed. Rep. of Germany

[21] Appl. No.: 437,398

[22] Filed: Oct. 28, 1982

[30] Foreign Application Priority Data

Nov. 12, 1981 [DE] Fed. Rep. of Germany ....... 3144874

[51] Int. Cl.³ .................. C07C 127/15; C07C 127/24
[52] U.S. Cl. ........................................ 528/68; 564/38; 564/47; 564/48; 564/50; 560/24; 560/157; 260/453 A
[58] Field of Search ...................... 528/68; 564/38, 47, 564/48, 50; 560/24, 157; 260/453 A

[56] References Cited

U.S. PATENT DOCUMENTS

| | | | |
|---|---|---|---|
| 2,888,439 | 5/1959 | Simons | 260/77.5 |
| 3,044,989 | 7/1962 | Shivers, Jr. | 260/77.5 |
| 3,184,502 | 5/1965 | Müller et al. | 260/482 |
| 3,385,829 | 5/1968 | Heydkamp et al. | 260/75 |
| 3,625,871 | 12/1971 | Traubel et al. | 260/2.5 AY |
| 3,682,867 | 8/1972 | Shackelford et al. | 528/68 |
| 3,808,250 | 4/1974 | Blahak et al. | 260/455 R |
| 3,865,791 | 2/1975 | Brinkmann et al. | 260/77.5 |
| 4,129,741 | 12/1978 | Schmidt et al. | 560/50 |
| 4,153,801 | 5/1979 | Schmidt et al. | 548/312 |
| 4,163,831 | 8/1979 | Gessell | 526/153 |
| 4,169,206 | 9/1979 | Mazánek et al. | 560/50 |
| 4,180,644 | 12/1979 | Marquis et al. | 528/68 |
| 4,224,417 | 9/1980 | Hajek et al. | 521/166 |
| 4,264,519 | 4/1981 | Hennig et al. | 260/453 A |
| 4,386,218 | 5/1983 | Rasshofer et al. | 564/38 |

FOREIGN PATENT DOCUMENTS 2948419 8/1981 Fed. Rep. of Germany .
1033912 6/1966 United Kingdom .
1117494 6/1968 United Kingdom .

OTHER PUBLICATIONS

H. John, J. Prakt Chemie, 130, pp. 314 et seq., pp. 323 et seq., 1931.

Primary Examiner—John Kight
Assistant Examiner—M. L. Moore
Attorney, Agent, or Firm—Gene Harsh; Joseph C. Gil

[57] ABSTRACT

This invention relates to an improved process for the preparation of aromatic polyamines containing urethane and/or biuret and/or urea and/or isocyanurate groups and preferably also ether groups by the hydrolysis of poly-N-monoaryl-N',N'-dialkyl urea compounds (1-aryl-3,3-dialkyl ureas). The ureas are obtained by the reaction of secondary aliphatic, cycloaliphatic or saturated heterocyclic amines with divalent to tetravalent isocyanate compounds containing isocyanate end groups attached to aromatic residues. The ureas correspond to the general formula:

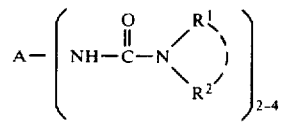

wherein $R^1$, $R^2$ denote alkyl or cycloalkyl groups, or together form a ring and A denotes a divalent to tetravalent residue attached to the ureas by aromatic groups.

Hydrolysis is carried out in the presence of water and up to two equivalents of a base containing hydroxide ions and/or up to two equivalents of a compound containing tertiary amino groups, optionally in the presence of solvents. The use of the polyamines obtained by this process for the synthesis of polyurethanes is also described.

11 Claims, No Drawings

PROCESS FOR THE PREPARATION OF POLYAMINES FROM N-MONOARYL-N',N'-DIALKYL UREA COMPOUNDS AND THEIR USE FOR THE SYNTHESIS OF POLYURETHANES

This invention is directed to an improved process for the preparation of aromatic polyamines containing urethane and/or biuret and/or urea and/or isocyanurate groups and preferably also ether groups by the hydrolysis of N-monoaryl-N',N'-dialkyl urea compounds (1-aryl-3,3-dialkyl ureas). The ureas are obtained by the reaction of secondary aliphatic, cycloaliphatic or saturated heterocyclic amines with divalent to tetravalent isocyanate compounds having isocyanate end groups attached to aromatic residues, and they correspond to the general formula:

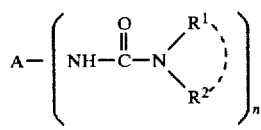

wherein
$R^1$, $R^2$ denote alkyl or cycloalkyl groups, or together form a ring,
A denotes a divalent to tetravalent residue attached to the ureas by aromatic groups, and
n denotes an integer of from 2 to 4.

Hydrolysis is carried out in the presence of water and up to 2 equivalents of a base containing hydroxide ions and/or up to 2 equivalents of a compound containing tertiary amino groups, optionally in the presence of solvents. The use of the polyamines obtained by this method for the synthesis of polyurethanes is also described.

BACKGROUND OF THE INVENTION

It is known that aromatic isocyanates may be converted into primary amines by acid hydrolysis. This reaction is only partially complete, however, since the amine obtained from hydrolysis reacts with unreacted isocyanates to form the corresponding urea. This secondary reaction cannot be suppressed by using an excess of a strong mineral acid. A comparatively recent example is found in Japanese Pat. No. 55007-827.

It is also known that aromatic isocyanates may be converted into aromatic amines by basic hydrolysis. The conditions for this hydrolysis, mentioned for two particular heterocyclic isocyanic acid esters in H. John, J. Prakt. Chemie, 130, 314 et seq (1931) and H. John, J. Prakt. Chemie, 130, 323 et seq (1931), are, however, completely unsuitable for the conversion of isocyanate prepolymers into the corresponding polyamines.

Processes by which carbamate salts obtained by the reaction of isocyanate compounds with aqueous bases may be converted into the free amino compounds by acidolytic decomposition with mineral acids or strong organic acids are described in German Offenlegungsschriften Nos. 2,948,419 and 3,039,600. One disadvantage of these processes is that they inevitably give rise to, for example, mineral acid salts, the removal of which renders the said processes less economical.

A process for the preparation of specific primary aromatic amines containing polyalkylene glycol ether segments is described in German Auslegeschrift No. 1,270,046. In this process, the reaction products of aromatic di- or triisocyanates with polyalkylene glycol ethers and/or polyalkylene glycol thioethers, preferably those with molecular weights of from 400 to 4,000, are reacted with secondary or tertiary carbinols and the reaction product is subsequently subjected to decomposition by heat in an inert solvent (optionally in the presence of acid catalysts). The disadvantage of this process, however, is that the thermal cleavage of urethanes is accompanied by the formation of combustible, readily-volatile alkenes which are explosive when mixed with air, necessitating that special safety measures be taken.

German Auslegeschrift No. 1,694,152 relates to the preparation of prepolymers having at least two amino end groups by the reaction of hydrazine, aminophenyl ethylamine or other diamines with an isocyanate prepolymer obtained from a polyether polyol and polyisocyanate (NCO:NH ratio=1:1.5 to 1:5). Any unreacted amine must be carefully removed by a separate process step, however, since it both powerfully catalyzes the reaction with polyisocyanates (thereby shortening the time available for processing) and itself enters into reactions.

Another possible method of synthesizing polyamines containing urethane groups is described in French Pat. No. 1,415,317. Isocyanate prepolymers containing urethane groups are converted into N-formyl derivatives by reaction with formic acid, and these derivatives are saponified to the aromatic amines with amino end groups. The reaction of isocyanate prepolymers with sulfamic acid according to German Auslegeschrift No. 1,155,907 also leads to compounds with amino end groups. Then, relatively high molecular weight aliphatic prepolymers containing secondary and primary amino groups are obtained according to German Auslegeschrift No. 1,215,373 by the reaction of relatively high molecular weight hydroxyl compounds with ammonia in the presence of catalysts under pressure at high temperatures, or according to U.S. Pat. No. 3,044,989 by the reaction of relatively high molecular weight polyhydroxyl compounds with acrylonitrile followed by catalytic hydrogenation. Relatively high molecular weight compounds containing terminal amino groups and urethane groups are also obtained according to German Auslegeschrift No. 2,546,536 or U.S. Pat. No. 3,865,791, by the reaction of isocyanate prepolymers with hydroxyl-containing enamines, aldimines or ketimines followed by hydrolysis. The main advantage of these methods is that, for example, although the aromatic amine released by hydrolysis reacts, for example, with the ketimine-isocyanate adduct to form urea, that hydrolysis, in most cases, proceeds very slowly.

Another possibility for synthesizing aromatic polyamines containing urethane and ether groups lies in ring opening, such as takes place in the reaction of isatoic acid anhydride and diols. Polyamines of this kind have been described, for example, in U.S. Pat. No. 4,180,644 and German Auslegeschriften Nos. 2,619,840; 2,648,774; 2,648,825; and 2,019,432. One disadvantage of this method, however, for many purposes, is the low reactivity of aromatic ester amines obtained by such a method.

The reaction of nitroaryl isocyanates with polyols followed by reduction to amines is also known (U.S.

Pat. No. 2,888,439), but the main disadvantage of this method is the high cost of the reduction step.

It has now surprisingly been found that specific aromatic polyamines containing urethane and/or urea and/or biuret and/or isocyanurate groups and preferably also ether groups (or other groups, e.g., acetal, thioether, dimethyl siloxane or polybutadiene groups) are obtained when certain ureas described in more detail below are treated with a base, preferably in equivalent or slightly excess quantities, based on the quantity of urea groups present.

It is surprising that the basic hydrolysis of the urea groups, substituted according to the invention, proceeds so selectively on urea partial structures substituted with aliphatic or cycloaliphatic groups, that any urethane and/or biuret and/or allophanate and/or isocyanurate groups present at the same time are not split. This would not have been expected from the published state of the art. It is also surprising that the hydrolysis of monomeric low molecular weight monoureas, which is known, may also be directly applied to high molecular weight polyurea compounds.

It is advantageous that in contrast to known methods of hydrolysis of isocyanate compounds by the preliminary reaction of the isocyanate compound with secondary amines, which leads quantitatively to urea compounds, no chain lengthening, by way of an isocyanate-water reaction, occurs in this case. Furthermore, the N',N'-dialkyl urea derivatives are relatively stable derivatives of the isocyanate prepolymers which are themselves, in many cases, not stable in storage, so that these derivatives may subsequently be converted into the desired polyamines at any time after their preparation.

DESCRIPTION OF THE INVENTION

The present invention relates to a process for the preparation of aromatic polyamines containing urethane and/or urea and/or biuret and/or allophanate and/or isocyanurate groups and preferably also ether groups, characterized in that a compound corresponding to the general formula:

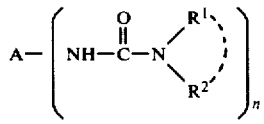

wherein
- A is a residue with a valency n, such as may be obtained by the removal of n isocyanate groups from an isocyanate compound having aromatically-bound isocyanate groups, and containing urethane and/or urea and/or biuret and/or allophanate and/or isocyanurate, and especially also ether groups, and preferably an isocyanate prepolymer based on aromatic polyisocyanates,
- $R^1$ and $R^2$ denote, independently of each other, linear, branched or cyclic saturated hydrocarbon groups containing 1 to 10 carbon atoms, or $R^1$ and $R^2$ may together form a ring with 4 to 6 carbon atoms, and
- n denotes an integer of from 2 to 4, is subjected to a basic hydrolysis in which carbon dioxide is split off.

The present invention also relates to a process for the preparation of aromatic polyamines containing urethane and/or urea and/or biuret and/or allophanate and/or isocyanurate groups and preferably also ether groups, characterized in that a compound corresponding to the general formula:

$$A(NCO)_n$$

wherein
- A denotes a residue such as may be obtained by the removal of n isocyanate groups from an isocyanate compound having isocyanate groups which are attached to aromatic residues, and containing urethane and/or urea and/or biuret and/or allophanate and/or isocyanurate groups and preferably ether groups, and
- n denotes an integer of from 2 to 4, optionally in the form of a solution in a solvent which is inert towards isocyanate groups, is treated, preferably, at from 0° to 60° C., with a mixture of
  (a) water,
  (b) from 0.1 to 10 equivalents (based on 1 isocyanate equivalent) of a secondary amine of the general formula:

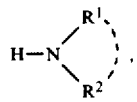

wherein
$R^1$ and $R^2$ denote, independently of each other, linear or branch chain aliphatic or cycloaliphatic saturated hydrocarbon groups having from 1 to 10 carbon atoms, or together, denote a heterocyclic ring containing 4 to 6 carbon atoms,
  (c) 0 to 2 equivalents (based on 1 isocyanate equivalent) of a base containing hydroxide ions,
  (d) 0 to 2 equivalents (based on 1 isocyanate equivalent) of a compound containing tertiary amino groups, and
  (e) 0 to 100 parts (based on 1 part of the compound $A(NCO)_n$) of a solvent, wherein A and n have the meaning defined above, and at least one of components (c) and (d) is used in a quantity amounting to 0.1 to 2 equivalents, preferably 0.8 to 1.8 equivalents, most preferably 1.0 to 1.5 equivalents, and the resulting aromatic polyamine is isolated from the reaction product in a known manner.

The invention further relates to the use of the aromatic polyamines obtainable by the process according to the invention for the preparation of optionally-cellular polyurethanes and polyurethane foams by the reaction of
  (a) polyisocyanates with
  (b) polyamines and, optionally,
  (c) other low molecular weight and/or relatively high molecular weight compounds having isocyanate reactive groups, and other known auxiliary agents and additives, characterized in that the substances used as the polyamine component are the polyamines prepared by the process according to the invention.

The isocyanate compounds $A(NCO)_n$ used in the process according to the invention are prepared in a known manner by the reaction of water and/or high molecular weight and/or low molecular weight compounds containing hydroxyl and/or amino and/or thiol groups (with molecular weights of from 60–12,000), with an excess of polyisocyanate.

The polyisocyanates used here may, in principle, be any aromatic or hetero aromatic polyisocyanates, such as, for example, 1,3- and 1,4-phenylene diisocyanate, 2,4- and 2,6-tolylene diisocyanate and any mixtures of these isomers, diphenyl methane-2,4'- and/or -4,4'-diisocyanate, including its alkyl- and chloro-substituted derivatives, and naphthylene-1,5-diisocyanate.

The following aromatic polyisocyanates, for example, may also be used: triphenylmethane-4,4',4''-triisocyanate; polyphenyl-polymethylene-polyisocyanates, such as may be obtained by aniline-formaldehyde condensation followed by phosgenation, as described, for example, in British Pat. Nos. 874,430 and 848,671; m- and p-isocyanatophenyl sulphonyl isocyanates according to U.S. Pat. No. 3,454,606; and perchlorinated aryl polyisocyanates, such as those described, for example, in German Auslegeschrift No. 1,157,601 (U.S. Pat. No. 3,277,138). Additional suitable aromatic polyisocyanates include polyisocyanates containing isocyanurate groups as described, for example, in U.S. Pat. No. 3,001,973 and German Pat. No. 1,022,789, No. 1,222,067, No. 1,027,394, No. 1,929,034 and No. 2,004,048; polyisocyanates containing urethane groups, as described, for example, in Belgian Pat. No. 752,261, or in U.S. Pat. Nos. 3,394,164 and 3,644,457; polyisocyanates containing acylated urea groups according to German Pat. Nos. 1,230,778; polyisocyanates prepared by telomerization reactions as described, for example, in U.S. Pat. No. 3,654,196; as well as uretdione polyisocyanates and isocyanurate polyisocyanates. The aromatic polyisocyanates containing sulphur, obtainable according to German Auslegeschrift No. 2,922,966, are also suitable starting polyisocyanates.

The distillation residues still containing isocyanate groups from the commercial production of isocyanates may be used, optionally dissolved in one or more of the above-mentioned polyisocyanates. Mixtures of the above-mentioned polyisocyanates may also be used.

It is generally preferred to use commercially available polyisocyanates, such as 2,4- and 2,6-tolylene diisocyanate and mixtures of these isomers ("TDI"), polyphenyl-polymethylene polyisocyanates which may be obtained by aniline formaldehyde condensation followed by phosgenation ("crude MDI"), and in particular, polyisocyanates containing urethane groups, isocyanurate groups or urea groups ("modified polyisocyanates"), in particular those modified polyisocyanates derived from 2,4- and/or 2,6-tolylene diisocyanate or from 4,4'- and/or 2,4'-diphenylmethane diisocyanate.

The isocyanate compounds (A(NCO)$_n$) are preferably prepared from compounds with molecular weights of from 400 to 12,000, in particular of from 400 to 6,000, which have at least 2, preferably 2 to 4, and in particular 2 or 3, hydroxyl, amino and/or thiol groups (preferably hydroxyl groups) and are free from readily-hydrolyzed groups such as ester groups. The conventional polyacetals, polythioethers and, in particular, polyethers of polyurethane chemistry, for example, may be used.

The polyethers containing at least two, generally 2 to 8, preferably 2 to 4 hydroxyl groups suitable for the process according to the invention are of known type and may be obtained, for example, by the polymerization of epoxides, such as ethylene oxide, propylene oxide, butylene oxide, tetrahydrofuran, styrene oxide or epichlorohydrin, on their own, for example, in the presence of Lewis catalysts, such as BF$_3$. These suitable polyethers may also be prepared by addition of the above epoxides, preferably ethylene oxide and propylene oxide, as mixtures or successively, to starting components containing reactive hydrogen atoms, such as water, alcohols, ammonia or amines, e.g., ethylene glycol, propylene glycol-(1,3) or -(1,2), trimethylol propane, glycerol, sorbitol, 4,4'-dihydroxy-diphenyl propane, aniline, ethanolamine or ethylene diamine. Sucrose polyethers, such as those described, for example, in German Auslegeschriften Nos. 1,176,358 and 1,064,938 and polyethers, started on formitol or formose (German Auslegeschriften Nos. 2,639,083 and 2,737,951), may also be used according to the invention. It is frequently preferred to use polyethers which contain predominantly primary OH groups (up to 90% by weight, based on all the OH groups present in the polyether).

Among the polythioethers may be particularly mentioned the products obtained by the condensation of thiodiglycol either on its own and/or with other glycols.

Polyhydroxyl compounds already containing urethane or urea groups and modified or unmodified natural polyols may be used according to the invention, as may products of the addition of alkylene oxides to phenol formaldehyde resins or to urea formaldehyde resins.

The above-mentioned polyhydroxyl compounds may also be variously modified before use. Thus, according to Offenlegungsschriften Nos. 2,210,839 (U.S. Pat. No. 3,849,515) and 2,544,195, a mixture of various polyhydroxyl compounds may be condensed by etherification in the presence of a strong acid to form a relatively high molecular weight polyol built up of various segments connected by ether bridges. Amide groups may also be introduced into the polyhydroxyl compounds, for example, according to German Offenlegungsschrift No. 2,559,372.

Representatives of the above-mentioned compounds to be used according to the invention have been described, for example, in High Polymers, Volume XVI, "Polyurethanes, Chemistry and Technology", by Saunders & Frisch, Interscience Publishers, New York, London, Volume I, 1962, pages 32 to 42 and pages 44 to 54 and Volume II, 1964, pages 5 and 6 and 198 to 199, and in Kunststoff Handbuch, Volume VII, Vieweg-Hochtlen, Carl Hanser Verlag, Munich, 1966, e.g. on pages 45 to 71. Mixtures of the above-mentioned compounds containing at least 2 isocyanate-reactive hydrogen atoms and having molecular weights of from 400 to 12,000 may, of course, be used, including, for example, mixtures of various polyethers.

The compounds containing at least 2 isocyanate-reactive hydrogen atoms used as starting materials for the preparation of the isocyanate compounds for the process according to the invention may also consist of, or contain, a proportion of relatively low molecular weight compounds of this kind, with molecular weights of from 18 to 399, preferably of from 60 to 399. These components include compounds containing water and-/or hydroxyl groups and/or amino groups and/or thiol groups, preferably hydroxyl groups, of the kind known from polyurethane chemistry as chain lengthening agents or cross-linking agents. These compounds generally contain from 2 to 8, preferably 2 to 4 isocyanate-reactive hydrogen atoms.

These components may also be used as mixtures of various compounds with molecular, weights of from 18 to 399, which contain at least 2 isocyanate-reactive hydrogen atoms. Examples of such compounds include water, ethylene glycol, propane diol-(1,2) and -(1,3), butanediol-(1,4) and -(2,3), pentanediol-(1,5), hexanediol-(1,6), octanediol-(1,8), neopentyl glycol, 1,4-bishydroxymethyl-cyclohexane, 2-methyl-1,3-propanediol, dibromobutenediol (U.S. Pat. No. 3,723,392), dianhydromannitol and dianhydrosorbitol, glycerol, trimethylol propane, hexanetriol-(1,2,6) and trimethylol ethane. Additional suitable examples include pentaerythritol, quinitol, mannitol and sorbitol, castor oil, di-, tri- and tetraethylene glycol, di-, tri- and tetrapropylene glycol, dibutylene glycol and higher polyethylene, polypropylene or polybutylene glycols with molecular weights of up to 399, 4,4'-dihydroxydiphenyl propane, dihydroxymethyl-hydroquinone, ethanolamine, diethanolamine, N-methyl-diethanolamine, triethanolamine and 3-aminopropanol.

The low molecular weight polyols used may also be mixtures of hydroxyaldehydes and hydroxyketones ("formoses") or the polyhydric alcohols ("formitol") obtained from them by reduction, such as the compounds obtained from the autocondensation of formaldehyde hydrate in the presence of metal compounds as catalysts and of compounds capable of enediol formation as co-catalysts (German Auslegeschriften Nos. 2,639,084; 2,714,084; 2,714,104; 2,271,186; 2,738,154; and 2,738,512).

Aliphatic diamines suitable according to the invention include, for example, ethylene diamine, 1,4-tetramethylene diamine, 1,6-hexamethylene diamine, 1,12-dodecamethylene diamine and mixtures thereof and 1-amino-3,3,5-trimethyl-5-aminomethyl cyclohexane ("isophorone diamine"). Further examples include 2,4- and 2,6-hexahydrotolylene diamine and mixtures thereof, perhydro-2,4'- and -4,4'-diaminodiphenyl methane, p-xylylene diamine, bis-(3-aminopropyl)-methylamine, diaminoperhydroanthracenes (German Auslegeschrift No. 2,638,731) and cycloaliphatic triamines, according to German Auslegeschrift No. 2,614,244. Hydrazine and substituted hydrazines, e.g., methyl hydrazine, may also be used according to the invention.

Examples of aromatic diamines include the diamines containing ether groups according to German Auslegeschrift No. 1,770,525 and 1,809,172 (U.S. Pat. Nos. 3,654,364 and 3,736,295), 2-halogen-1,3-phenylene diamines, optionally substituted in the 5-position (German Auslegeschrift Nos. 2,001,772; 2,025,896; and 2,065,869) and 3,3'-dichloro-4,4'-diamino-diphenyl methane. Additional suitable aromatic diamines include tolylene diamine, 4,4'-diamino-diphenyl methane, 4,4'-diamino-diphenyl disulphides (German Auslegeschrift No. 2,404,976), diaminodiphenyl dithioether (German Auslegeschrift No. 2,509,404), aromatic diamines substituted by alkyl thio groups (German Auslegeschrift No. 2,638,760), aromatic diamines containing sulphonate or carboxylate groups (German Auslegeschrift No. 2,720,166) and the high melting diamines mentioned in German Auslegeschrift No. 2,635,400. The amino alkylthio anilines according to German Auslegeschrift No. 2,734,574 represent examples of aliphatic-aromatic diamines which are also suitable according to the invention.

The prepolymers containing free isocyanate groups are prepared in the known manner by the reaction of the components either solvent-free or in solution. The equivalent ratio of isocyanate groups to active hydrogen atoms (preferably OH groups) is, in all cases, greater than 1 and should, in general, be in the range of 1.5:1 to 2.8:1, although a greater excess of polyisocyanate may, of course, be used. The prepolymers generally have an oily-to-waxy consistency, depending on the starting components used. If the NCO/OH ratio is greater than 2, the prepolymers obtained are, on the whole, not lenthened, whereas NCO/OH ratios below 2 may result in an increase in the average molecular weight of the prepolymers.

As already mentioned above, a proportion of low molecular weight polyols may also be included as chain-lengthening agents, in addition to the relatively high molecular weight starting compounds for the preparation of the prepolymers. Relatively high molecular weight prepolymers are obtained also in this case. If the isocyanate prepolymers contain additional groups, e.g., carbodiimide, acyl urea or uretone imine groups, these may also be present in the products according to the invention.

For the process according to the invention, it is preferred to use prepolymers obtained from relatively high molecular weight polyether glycols (optionally with the inclusion of chain-lengthening agents of the type described above) and aliphatic and/or aromatic diisocyanates in an equivalent ratio in the range of 1:1.5 to 1:2.0, in particular, about 1:2.

Examples of suitable secondary amines of the general formula:

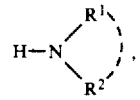

for the process according to the invention, include dimethylamine, diethylamine, di-i-propylamine, diisobutylamine, di-n-propylamine, di-n-butylamine, di-sec.-butylamine, di-iso-amylamine, di-n-octylamine, di-2-ethyl-hexylamine and di-n-nonylamine. Less suitable are compounds having 2 or more secondary amino groups, e.g., N,N'-dimethyl-ethylene diamine, N,N'-dimethyl hexane-1,6-diamine, N,N'-dimethyl butane-1,4- diamine and N,N',N''-trimethyl-diethylene triamine.

Secondary amines containing different substituents, such as methyl propylamine or compounds which have a secondary and a tertiary amino group in the same molecule, e.g., trimethyl ethylene diamine, are also suitable, but less preferred, for reasons of accessibility.

Suitable bases for use according to the invention include organic and inorganic compounds containing or forming hydroxide ions. Inorganic alkali metal and alkaline earth metal hydroxides, alkali metal carbonates and bicarbonates and alkaline earth metal oxides are preferred, with sodium and potassium hydroxide being particularly preferred, but suitable organic bases, such as tetraalkyl ammonium hydroxides, and trialkyl ammonium hydroxide residues fixed to an insoluble polymer skeleton may also be used.

Numerous series of products are suitable as compounds containing tertiary amino groups, and include, for example, simple trialkylamines containing identical or different substituents, such as triethylamine, tri-i-propylamine, tri-iso-butylamine and cyclohexyl-di-i-propylamine. Peralkylated polyamines are also suitable, e.g., tetramethyl ethylene diamine, tetramethyl butylene diamine, tetramethyl hexylene diamine, permethyl diethylene triamine, permethyl dipropylene triamine, permethyl triethylene tetramine, 1,4-dimethyl-piperazine, 1-methyl-4-(2-dimethylaminoethyl)-piperazine, N-(2-dimethylaminoethyl)-morpholine, bis-(2-diethylaminoethyl)-ether, bis-(2-dimethylaminopropyl)-ether and diazabicyclo-octane. Also suitable according to the invention, but less preferred, are the aromatic and heteroaromatic amines such as N,N-dimethyl aniline, N,N-dimethyl-o-toluidine or pyridine, picoline, lutidines or amidines, such as diazabicycloundecene.

In the General Method (Variation A) for carrying out the process according to the invention, the required urea is first prepared by the addition of a secondary amine, of the type exemplified above, to an isocyanate compound which may be present in the pure form or dissolved in or as a mixture with an isocyanate-inert solvent. Examples of suitable solvents include dichloromethane, trichloromethane, tetrachloromethane, 1,1,1-trichloroethane, cyclohexane, methylcyclohexane, hexane, diethyl ether, benzene and toluene, but water-miscible solvents, such as dimethoxy ethane, tetrahydrofuran and dioxane are preferred. On the whole, however, the use of solvents for the isocyanate prepolymer is less preferred.

The secondary amine, which is preferably added at approximately room temperature, is introduced either in the pure form or as a mixture with or in solution with a suitable solvent, preferably water. The secondary amine is used in a quantity at least equimolar to the isocyanate groups present so that the equivalent ratio is $NH:NCO \geq 1$. An excess of amine (e.g., $NH:NCO = 2:1$) may also be useful in order that the excess secondary amine concurrently function as a diluent.

The reaction resulting in ureas accompanied by the evolution of heat, with external cooling ensuring that the temperature does not exceed about 60° to 70° C. The urea compounds, which are preferred for the process according to the invention, are resinous-to-liquid compounds which are soluble in organic solvents.

When the urea reaction mixture no longer has any measurable isocyanate content, water is added, if addition of the amine to the isocyanate compound present was not carried out in an aqueous media. At least 1 mol of water is used per mol of urea groups present, but an excess, e.g., a 1.1 to 100 times excess, is preferred.

Base is then added to this reaction mixture which, in addition to the urea compound and water, may contain other solvents and diluents, as well as emulsifiers to improve the amine/NCO compound reaction. Catalytic quantities of $OH^{\ominus}$ ions have no effect since they are converted into inactive $HCO_3^{\ominus}$ anions. Tertiary amines may successfully be used in catalytic or substoichiometric quantities (based on the quantity of urea groups), however, but the reaction velocity is relatively low, making the volume/time yields unfavorable. Since distillation is necessary anyway, to work up the reaction product, the use of less-than-stoichiometric quantities of compounds containing tertiary amino groups does not provide any particular advantages.

It is therefore essential in the case of compounds containing hydroxide ions and preferably in the case of compounds containing tertiary amino groups to use at least stoichiometric quantities of base (based on the quantity of urea groups). A small excess of base may be used for safety, but there is no advantage in using a large excess.

Hydrolysis, which is accompanied by the evolution of $CO_2$, is carried out at a reaction temperature of approximately 40° to 100° C., preferably 80° to 100° C., and when stoichiometric quantities of base are used, the reaction is generally completed after 15 minutes to 6 hours, in most cases 30 minutes to 2 hours. When using catalytic quantities (0.001–0.1 equivalents of t-amine to 1 equivalent of urea groups) and less than stoichiometric quantities of compounds containing t-amino groups (e.g., 0.1 to 0.5 equivalents of t-amino groups to 1 equivalent of urea groups), the reaction takes up to 12 days.

After termination of the reaction, the product is generally worked-up by distilling off, preferably at reduced pressure (e.g., 13 to 900 mbar), the secondary amine obtained from hydrolysis, water and/or any tertiary amine present. The products distilled off are preferably prepared for further use, and any solid substances (e.g., sodium and potassium carbonates and bicarbonates) present in the reaction product are filtered off. This completes the working-up process.

Hydrolysis and working-up may also be combined, by distilling off the released diamine during hydrolysis. This, of course, can only be carried out if the secondary amine and the water/tertiary amine mixture can be separated to a sufficient extent by distillation.

The end of the reaction or complete conversion of the urea groups into amine units may be observed, for example, from the quantity of secondary amine, the quantity of carbon dioxide evolved and the disappearance of the urea band from the IR spectrum.

In a modification (Variation B) of the process according to the invention, the urea which is to be hydrolyzed is produced in situ. Use is made of the fact that aromatic isocyanates generally react more rapidly with secondary amines at 20° to 100° C. than with water to form ureas or with hydroxide groups to form carbamates. When this variation of the process is employed, however, it is necessary to ensure that sufficient secondary amine is always available for the reaction with the isocyanate groups of the isocyanate compound. A sufficient quantity of secondary amine may be ensured, (i) by initially introducing a stoichiometric quantity of secondary amine (equivalent ratio of $NH:NCO$ of $\geq 1$) into the reaction vessel of (ii) by carrying out the formation of urea under conditions providing for rapid hydrolysis of the urea compound with liberation of the secondary amine which may, in turn, be used again for the formation of urea by reaction with more isocyanate.

In the process according to the invention, when a stoichiometric quantity of secondary amine is introduced into the reaction vessel (situation (i)), the isocyanate prepolymer is generally used without solvent, although solutions of isocyanate prepolymers in isocyanate-inert solvents (which are preferably also miscible with water), may also be used, e.g., for lowering the viscosity. Suitable solvents for this purpose include, for example, dimethoxyethane, diethylene glycol dimethyl ether, dioxane and tetrahydrofuran; less suitable solvents include, for example, hydrocarbons, chlorinated hydrocarbons and lower aromatic compounds, as well as chlorinated and nitrogenated aromatic compounds. The isocyanate prepolymers are preferably used in the form of solutions in the abovementioned solvents if they are solid, or if they are non-melting, or difficult to melt at 20° to 80° C. or if the form viscous liquids.

If pure liquid isocyanate prepolymers, which are not in solution, are used in the process according to the invention, they are preferably at a temperature of from 20° to 80° C., more particularly of from 40° to 70° C. If the isocyanate prepolymers are used in the form of solutions, containing, e.g., from 1 to 400 parts of isocyanate prepolymer per 100 parts of solvent, the temperature is preferably from 20° to 40° C., but not higher than the boiling point of the solvent.

The isocyanate compounds are mixed with a basic medium, containing water, preferably ≧1 part of water to 1 part of isocyanate compound; bases containing OH⊖ groups and/or compounds containing tertiary amino groups; a secondary aliphatic amine; and optionally a solvent, which is maintained at 0° to 60° C. The bases containing OH⊖ groups may be organic or inorganic compounds containing hydroxide groups. They are preferably inorganic alkali metal and alkaline earth metal hydroxides, most preferably sodium and potassium hydroxide, but may also be organic bases, such as tetraalkyl ammonium hydroxides or basic ion exchangers containing trialkyl ammonium hydroxide groups attached to an insoluble polymer skeleton. These bases are used in quantities corresponding to 0 to 2 OH⊖ groups, preferably 0.1 to 1.8 OH⊖ groups, most preferably 1.00 to 1.5 OH⊖ groups to 1 isocyanate group (based on the 1-aryl-3,3-dialkyl-urea group, which forms in the course of the reaction with the secondary amine). If these bases are used in a quantity providing from 0.1 to 0.99 OH⊖ groups to 1 isocyanate group, another compound containing tertiary amino groups is also used. Using bases in OH⊖:NCO proportions of 0.1 to 0.99 is, however, less preferred on the whole since urea hydrolysis then proceeds very slowly, especially at the lower range of base concentration, and filtration is always necessary. It is preferred to use a quantity of bases containing OH⊖ groups which is equivalent to or slightly greater than the quantity of 1-aryl-3,3-dialkyl urea groups.

The basic medium may also contain compounds having tertiary amino groups. These may be used alternatively to the bases containing OH⊖ groups and, indeed, must be present when no bases containing OH⊖ groups are used, but may also be used in any mixture with them. The same quantities are preferred as with the use of bases containing OH⊖ ions, the quantities being based on the quantity of t-amino groups present. Suitable compounds containing t-amino groups have already been mentioned.

The compounds containing t-amino groups may be added in the pure form (liquid or solid), or as solutions. Water is the preferred solvent, but solvents which react neither with isocyanate groups nor with secondary amines and are water soluble may also be used. Suitable solvents of the kind include (apart from water) dioxane, tetrahydrofuran, ethanediol-1,2-dimethylether and 3-oxa-pentane-1,5-diol-dimethylether (Diglyme). A solvent may be used, for example, in a quantity of from 0.5 to 100 parts to 1 part of a compound containing tertiary amino groups.

The use of bases containing OH⊖ groups is generally preferred to the use of compounds containing t-amino groups or mixtures of compounds containing t-amino groups and bases containing OH⊖ groups.

Suitable secondary amines have already been listed. Secondary amines particularly suitable for this variation of the process according to the invention include relatively volatile amines, such as dimethylamine, diethylamine, di-n-propylamine, diethylamine, di-n-propylamine, di-i-propylamine, di-n-butylamine, di-i-butylamine and di-sec.-butylamine, dimethylamine being particularly suitable and preferred.

In this variation of the process, the secondary amines were used in stoichiometric quantities or in excess, based on the quantity of isocyanate groups (NCO:NH=1:1 to 1:1.1), although a large excess may also be used (NCO:NH=1:1 to 1:10), in which case the secondary amine functions as a diluent.

Another solvent which is preferably immiscible with water, e.g., dioxane, tetrahydrofuran or dimethoxyethane, may be added before addition of the isocyanate prepolymer or at any stage of the reaction to lower the viscosity of the mixture. For example, from 10 to 1,000 parts of cosolvent may be used with 100 parts of water.

In the process according to the invention, the isocyanate prepolymers are slowly combined with the basic medium, for example, with the aid of a dropping funnel, or by mechanical injection from a nozzle or by countercurrent injection. The time taken to combine the basic medium with the isocyanate prepolymer depends on the amount of heat evolved in the reaction. Cooling must be provided to ensure that the temperature in the reaction vessel does not exceed the temperature ranges indicated above. This is particularly important in the case of trifunctional and higher-functional isocyanate prepolymers and if the process is not carried out continuously.

Additional solvent may be added when all the isocyanate prepolymer has been added, although this is generally not necessary. Suitable solvents apart from those mentioned above include, e.g., water-soluble alcohols such as methanol, ethanol, i-propanol and glycol monomethylether, as well as, for example, acetonitrile and nitromethane. Solvents which are immiscible with water, such as, for example, ether, cyclohexane, and toluene, are less suitable.

Following one method of purification, the resulting suspension and/or solution of urea is adjusted to a temperature at which reflux takes place, e.g., 80° to 100° C. The reaction mixture is heated with reflux for a period of from 3 hours to 10 days, preferably 6 hours to 2 days, and freed from all volatile constituents by fractional distillation. The secondary amine and/or compound containing tertiary amino groups may be recovered from the distillate by known methods. This distillation may be carried out at normal pressure or reduced pressure, e.g., at 13 to 910 mbar.

An oil pump vacuum (0.13 to 7 mbar) is advantageously then applied, at an elevated temperature (80° to 100° C.), to remove the last traces of volatile constituents.

Any salts precipitated, e.g., carbonic acid salts, are removed from the distillation residue while still hot (40° C. to 100° C.) by filtration or suction filtration, preferably using a pressure suction filter, optionally one which may be heated.

Alternatively, the urea reaction mixture is preferably not heated under reflux but instead, the volatile constituents, in particular the secondary amines split off, are distilled off during the reaction. The progress of the reaction may be monitored from the quantity of secondary amine recovered. This variation is particularly suitable with dimethylamino- and diethylamino-urea compounds are present, whereas in the presence of other secondary amine urea components it is sometimes necessary to add more solvent (water) during the reaction to keep the mixture stirrable. This variation is also particularly suitable when using only non-volatile alkali metal hydroxides as bases, while compounds containing t-amino groups are sometimes distilled off at the same time.

This variation is preferably carried out at 80° to 100° C. and without the application of a vacuum. After removal of the secondary amine by distillation at normal pressure, the other volatile components are distilled off at normal or reduced pressure, e.g., at 13.3 to 933 mbar and subsequently at, e.g., 0.13 to 13 mbar and at temperatures of from 40° to 100° C.

The carbonic acid salt is then filtered from the distillation residue while still hot (40° to 100° C.) or removed by suction filtration, using a pressure-suction filter (which is preferably heated).

If the product has very high viscosities, it may be necessary to dilute the carbonic acid salt containing mixture with an inert solvent, such as dichloromethane or toluene before suction filtration. This solvent is subsequently removed by distillation after the filtration is carried out.

In a modification of the process according to the invention, using sub-stoichiometric quantities of secondary amine (equivalent ratio NH:NCO<1) (situation (ii)), the isocyanate prepolymer is again generally used without solvent, although solutions of isocyanate prepolymers in isocyanate-inert solvents, which are preferably also water-miscible, may be used, for example, to lower the viscosity. Suitable solvents for this purpose include, e.g., dimethoxy ethane, diethylene glycol dimethyl ether, dioxane and tetrahydrofuran. Other solvents, e.g., hydrocarbons, chlorinated hydrocarbons and lower aromatic solvents, including chlorinated and nitrated aromatic solvents, are less suitable for this purpose. However, the isocyanate prepolymers are preferably used as solutions in the above-mentioned solvents if the prepolymers are solid substances or infusible, resistant to fusing or highly viscous at 20° to 80° C.

If pure, liquid isocyanate prepolymers not in the form of solutions are used in the process according to the invention, they are preferably at a temperature of from 20° to 80° C., particularly from 40° to 70° C. If the isocyanate prepolymers are used in dissolved form, the preferred temperature is from 20° to 40° C., but in any case, not higher than the boiling point of the solvent. If the isocyanate prepolymers are used as solutions, they may contain from 1 to 400 parts of isocyanate prepolymer to 100 parts of solvent.

The isocyanate compounds are mixed with a hot basic medium, containing water, preferably ≧1 part of water to 1 part of isocyanate compound, bases containing OH$^\ominus$ groups and/or compounds containing t-amino groups, a secondary aliphatic amine, and optionally, a solvent, which is kept under reflux at 60° to 100° C., preferably at 80° to 100° C. The bases containing OH$^\ominus$ groups and the compounds containing t-amino groups used in this variation of the process according to the invention have already been listed. They are preferably used in stoichiometric quantities (1 mol of OH$^\ominus$ or 1 mol of t-amino groups to 1 mol of NCO) or slightly excess quantities. In this case also, it is preferred to use bases containing OH$^\ominus$ groups rather than compounds containing t-amino groups.

The secondary amines used in this variation are the same as already mentioned above. For process technical reasons, dimethylamine and diethylamine are less preferred in this case. The secondary amines on the other hand, which are preferably not too readily-volatile, are in this case used in quantities providing from 0.05 to 0.99, preferably from 0.3 to 0.6 secondary amino groups for each isocyanate group of the isocyanate compound.

An isocyanate inert solvent which is preferably also water-miscible, e.g., dioxane, tetrahydrofuran or dimethyoxyethane, may be added either before the basic medium is combined with the isocyanate component or at any stage of the reaction in order to lower the viscosity. For example, from 10 to 1,000 parts of some other solvent or solvent mixture may be added to 100 parts of water.

The reaction is generally carried out by heating the reaction chamber containing water, bases and secondary amine to 20°–100° C., preferably to 80°–100° C., most preferably to 100° C. and maintaining this temperature throughout the reaction. This reaction mixture is then combined with a suitable quantity of isocyanate compound so that no free isocyanate groups are left after the isocyanate groups introduced have reacted with all the secondary amine molecules. The urea groups formed in the reaction are broken down again by the action of the base and the temperature in the reaction chamber. The desired aromatic amine is thus obtained, together with the original secondary amine which may be returned to the reaction with fresh isocyanate compound.

The mixture containing the bases is combined with the isocyanate component at the rate at which secondary amine is split off from urea to be available for further reaction. The required reaction time depends upon the concentration of the secondary amine, the reaction temperature and the ease with which the secondary amine is split off from the urea. Times ranging from 2 hours to 2 days are generally required to complete the reaction, with 6 hour to 18 hour times preferable.

After termination of the reaction, the secondary amine and the solvent are distilled off, respectively, for example, at 100° C./13.3 to 900 mbar and 100° C./0.13 to 13 mbar, and any carbonic acid salt which has precipitated is filtered off. This filtration is preferably carried out with a pressure-suction filter designed to be heated and is normally carried out at 60° to 100° C. With salts of very high viscosity, it may be advantageous to lower the viscosity of the precipitate with a diluent such as dichloromethane or toluene.

The polyamines obtained according to the invention are medium viscosity to high melting products. They have a total nitrogen content of about 38% to 0.5%, preferably 20% to 0.8%, and most preferably, from 4.3% to 1.2%. Their primary nitrogen content is from 19% to 0.25%, preferably from 10% to 0.4%, most preferably, from 2.15% to 0.6%.

Due to their low vapor pressure, the polyamines obtained according to the invention are advantageously used as reactants for polyisocyanates in the production of cellular or non-cellular polyurethanes, where they may, if desired, be combined with other low molecular weight (32 to 399) and/or relatively high molecular weight (400 to about 12,000) compounds containing isocyanate reactive groups. Suitable starting components for the production of polyurethanes have been mentioned above in connection with the preparation of the prepolymers and are also mentioned in German Offenlegungsschriften Nos. 2,302,564; 2,432,764 (U.S. Pat. No. 3,963,679); 2,639,083; 2,512,385; 2,513,815; 2,550,796; 2,550,797; 2,550,833; 2,550,860 and 2,550,862. These references also mention auxiliary agents and additives which may be used in the production of polyurethanes. The present invention also relates to the preparation of polyurethane ureas by means of the polyamines prepared according to the invention.

Other applications of the polyamines prepared according to the invention include, for example, their use as coupling components for diazo dyes and as hardeners for epoxide and phenol resins as well as their use in any other known reactions of amines such as, for example, the formation of amides or imides.

formed was investigated by gas chromatography for its liberated amine content.

The following results were obtained:

| Urea | Amine split off (Bp) (°C.) | Amine yield after 3 hours (%) |
|---|---|---|
| ⌬-N(H)-C(=O)-NH-CH₃ | H₂NCH₃* (−6) | 0 ** (Not according to the invention) |
| ⌬-N(H)-C(=O)-N(CH₃)₂ | HN(CH₃)₂ (7.4) | 98 ** (According to the invention) |
| ⌬-N(H)-C(=O)-N(H)(C₂H₅) | H₂NC₂H₅* (17) | 0 ** (Not according to the invention) |
| ⌬-N(H)-C(=O)-N(C₂H₅)₂ | HN(C₂H₅)₂ (56) | 84 (According to the invention) |
| CH₃NH-C(=O)-N(C₂H₅)₂ | HN(C₂H₅)₂ (56) | 0 (Not according to the invention) |

*prepared from methyl isocyanate or ethyl isocyanate and aniline.
**direct introduction of the gaseous distillate into dilute hydrochloric acid and back titration of the excess acid.

The following examples serve to illustrate the process according to the invention. Quantities given denote parts by weight or percentages by weight, unless otherwise indicated.

EXAMPLES

Example 1

This example demonstrates the resistance to basic hydrolysis of 1-aryl- and 1-alkyl-3,3-dialkyl-, -3-alkyl-, -3,3-diaryl- and -3-aryl ureas.

100 g of each of the urea compounds prepared from phenyl isocyanate or methyl isocyanate and various amines were heated to 100° C. with 10 g of water and 20 g of sodium hydroxide for 3 hours. Any distillate

Example 2

These examples demonstrate the resistance to basic catalysis of ureas obtained from diisocyanates and aromatic and aliphatic secondary amines.

2.1

100 g of each of the urea compounds prepared from tolylene diisocyanate or hexane-1,6-diisocyanate and various amines are heated to 100° C. with 20 g of sodium hydroxide and 40 g of water for 3 hours. Any distillate formed was investigated by titration or gas chromatography to determine the amount of amine split off.

The following results were obtained:

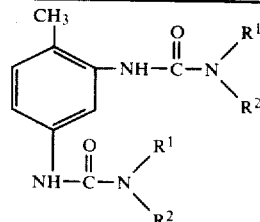

| Urea | Amine split off B.p. (°C.) | Amine yield after 3 hours at 100° C. (%) |
|---|---|---| aromatic isocyanate (according to the invention)

| | Primary Amines | (Not according to the invention) |
|---|---|---|
| R¹ = H, R² = CH₃* | H₂NCH₃ (−6) | 0** |
| R¹ = H, R² = C₂H₅* | H₂NC₂H₅ (17) | 0** |
| R¹ = H, R² = C₃H₇ | H₂NC₃H₇ (49) | 0** |
| R¹ = H, R² = i-C₃H₇ | H₂N—i-C₃H₇ (32) | 0** |
| | Secondary Amine | (According to the invention) |

-continued

| Urea | Amine split off B.p. (°C.) | Amine yield after 3 hours at 100° C. (%) |
|---|---|---|
| $R^1 = R^2 = CH_3$ | $HN(CH_3)_2$ (7.4) | 94% |
| $R^1 = R^2 = C_2H_5$ | $HN(C_2H_5)_2$ (56) | 78% |

$$R^1\diagdown\underset{R^2}{N}-\overset{O}{\underset{\|}{C}}-NH\text{-}(CH_2)_6\text{-}NH-\overset{O}{\underset{\|}{C}}-\underset{R^2}{N}\diagup R^1$$

aliphatic diisocyanate (not according to the invention)

| | | |
|---|---|---|
| $R^1 = H, R^2 = CH_3$* | $H_2NCH_3$ (−6) | 0** |
| $R^1 = H, R^2 = C_2H_5$* | $H_2NC_2H_5$ (17) | 0** |
| $R^1 = H, R^2 = i\text{-}C_3H_7$ | $H_2NiC_3H_7$ (32) | 0** |
| $R^1 = R^2 = C_2H_5$ | $HN(C_2H_8)_2$ (56) | 0 |

*prepared from methyl isocyanate or ethyl isocyanate and 2,4-diamino toluene.
**direct introduction of gaseous condensate into dilute hydrochloric acid and back titration of excess acid.

2.2

100 g of each of the urea compounds prepared from tolylene diisocyanate or hexane-1,6-diisocyanate with various primary and secondary amines were heated under reflux with 20 g of sodium hydroxide and 60 g of water. After 3 hours boiling under reflux, all the volatile substances were distilled off at 100° C./21 mbar and the amount of amine which had been split off was determined. A further 60 ml of water were then added and the reaction mixture was again kept under reflux for 3 hours and again distilled off and the amount of amine split off was determined.

The following results were obtained:

| Urea | Amine split off (Bp.) (°C.) | Amine yield after 3 hours and after 6 hours (%) | |
|---|---|---|---|

$$\text{CH}_3\text{-}\underset{\underset{NH-\overset{O}{\underset{\|}{C}}-N\diagdown R^2}{}}{\overset{NH-\overset{O}{\underset{\|}{C}}-N\diagup R^1}{\text{C}_6H_3}}$$

Aromatic isocyanate (according to the invention)

| Urea | Amine split off | 3 hr | 6 hr |
|---|---|---|---|
| $R^1 = H, R^2 = $ Cyclohexyl | ⟨cyclohexyl⟩-NH$_2$ (134.5) | 0 | 0 |
| | | (Not according to the invention) | |
| $R^1 = H, R^2 = C_6H_5$ | ⟨phenyl⟩-NH$_2$ (184) | 1 | 3 |
| | | (Not according to the invention) | |
| $R^1 = R^2 = n\text{-}C_4H_9$ | $HN(n\text{-}C_4H_9)_2$ (19) | 63 | 81 |
| | | (According to the invention) | |

$$R^1\diagdown\underset{R^2}{N}-\overset{O}{\underset{\|}{C}}-NH\text{-}(CH_2)_6\text{-}NH-\overset{O}{\underset{\|}{C}}-\underset{R^2}{N}\diagup R^1$$

Aliphatic diisocyanate basis (not according to the invention)

| Urea | Amine split off (Bp.) (°C.) | Amine yield after 3 hours and after 6 hours (%) | |
|---|---|---|---|
| $R^1 = H, R^2 = $ cyclohexyl | ⟨cyclohexyl⟩-NH$_2$ (134.5) | 0 | 0 |
| $R^1 = H, R^2 = C_6H_5$ | ⟨phenyl⟩-NH$_2$ (184) | 0 | 0 |

| | -continued | | |
|---|---|---|---|
| $R^1 = R^2 = $ n-$C_4H_9$ | HN($C_4H_9$)$_2$ (159) | 0 | 0 |

(Not according to the invention)

Example 3

Preparation of a linear diaminopolyether 3.1 Preparation of the urea 1,500 g of an isocyanate prepolymer with an isocyanate content of 3.6% (1.284 mol NCO) prepared from tolylene-2,4-diisocyanate and a polypropylene glycol ether diol having an average molecular weight of 2.000, in an NCO/OH-ratio of 2:1, are dissolved in 750 ml of anhydrous dioxane. 93.75 g (1.284 mol) of diethylamine are added within 30 minutes at a temperature not exceeding 40° C. The clear solution, which shows no free isocyanate groups in the IR spectrum, is then stirred for 15 minutes.

3.2 Preparation of the amine

The above reaction mixture is divided into three equal parts and worked-up by various methods.

3.2.1 Use of an equimolar quantity of potassium hydroxide 48 g of a 50% potassium hydroxide solution (containing 428 mmol of KOH) are added at 20° C. to 761 g of the above reaction mixture containing 425 mmol of urea groups. A color change to yellow occurs instantly. The reaction is then heated to 100° C. for 9 hours, during which time an aqueous azeotropic mixture containing diethylamine is distilled off. The end of the reaction is detected by determination of the amine content of the condensate by titration, and the volatile constituents of the reaction mixture are distilled off at 100° C./26 mbar. The reaction product is suction-filtered at 80° C. to free it from precipitated carbonic acid salt. A total of 30.3 g (97% of theoretical amount) of diethylamine is retained, with additional data below in Table 1.

3.2.2 Use of an equimolar quantity of compounds containing t-amino groups (diazabicyclooctane, "Dabco ®")

24 g of water and 24 g of diazabicyclooctane (214 mmol = 428 mmol of t-amino groups) are added to 761 g of the above reaction mixture at 20° C. and the mixture is heated to 100° C. until no more diethylamine can be detected in the condensate (total 20 hours). The resultant product is worked-up as under 3.2.1, and specific data is contained in Table 1.

3.2.3 Use of a sub-stoichiometric quantity of a compound containing tertiary amino groups 24 g of water and 2.4 g of diazabicyclooctane (21.4 mol) were added to 761 g of the above reaction mixture at 20° C. and the mixture was heated to 100° C. until no more diethylamine could be detected in the condensate (total 72 hours). Working-up, as under 3.2.1, with data in Table 1.

TABLE 1

| Data of Experiments 3.2.1, 3.2.2 and 3.2.3. | | | |
|---|---|---|---|
| Experiment | 3.2.1 | 3.2.2 | 3.2.3 |
| Yield (%) | 96 | 96 | 89 |
| NH number (mg KOH/g) | 43.4 | 40.0 | 38.8 |
| Acid number (mg KOH/g) | <0.05 | <0.05 | <0.05 |
| Molecular weight | 2900 | 3200 | 3400 |
| Viscosity (mPa · s) (at 75° C.) | 430 | 510 | 590 |
| Water content (%) | 0.11 | 0.08 | 0.08 |

TABLE 1-continued

| Data of Experiments 3.2.1, 3.2.2 and 3.2.3. | | | |
|---|---|---|---|
| Experiment | 3.2.1 | 3.2.2 | 3.2.3 |
| (Karl Fischer) | | | |

Example 4

Preparation of a linear diaminopolyether 4.1 Preparation of the urea 1,000 g of a prepolymer having an isocyanate content of 3.5%, which was prepared by the reaction of tolylene diisocyanate with a polypropylene glycol ether diol with average molecular weight 2,000, using an NCO:OH ratio of 2:1, is reacted with 118.3 g of diethylamine (1.62 mol) at room temperature to give rise to the corresponding liquid urea by an exothermic reaction.

4.2 Preparation of the amine

After 10 minutes stirring at the end of the reaction, the reaction mixture is diluted with 72 ml of 45% sodium hydroxide solution and heated to 100° C. for 6.5 hours, without distillation for the removal of the volatile components.

500 ml of toluene is added to the resulting product which is permeated with crystals, and the crystals are removed by suction filtration (sodium carbonate or bicarbonate). The filtrate containing toluene is freed from all volatile compounds by heating to 100° C. at 18 mbar and then at 100° C. at 1.33 mbar.

Product data:
Yield (%): 97
NH number (mg KOH/g): 44.1
Acid number (mg KOH/g): <0.05
Molecular weight: 2600
Viscosity (mPa.s) (at 75° C.): 445
Water content (%) (Karl Fischer): 0.1

Example 5

Preparation of a trifunctional polyether 5.1 Preparation of the urea 1000 g of an isocyanate prepolymer (isocyanate content 1.93%) which has been prepared from tolylene-2,4-diisocyanate and a polypropylene oxide/polyethylene (80/20) oxide block copolyether triol with an average molecular weight of 6,000 started on trimethylol propane, using an NCO:OH ratio of 2:1, are introduced into the reaction vessel. The liquid urea is prepared within 30 minutes, using 40.99 g of a 50.5% aqueous dimethylamine solution (containing 0.46 mol dimethylamine).

5.2 Preparation of the amine

After the above reaction mixture has been stirred for 15 minutes following the end of the reaction, 40.9 ml of 45% sodium hydroxide solution are added and the mixture is heated to 100° C. for 3 hours. Gaseous dimethylamine escapes during this time. The resulting product mixture is freed from water at 100° C./18 mbar and 100° C./1.33 mbar and when the oily liquid left behind has been cooled to 80° C., the carbonic acid salt present therein is removed by filtration with a pressure-suction filter.

Product data:

Yield (%): 93
NH number (mg KOH/g): 22
Acid number (mg KOH/g): 0.05
Molecular weight: 7000
Viscosity (mPa.s) (at 75° C.): 710
Water content (%) (Karl Fischer): 0.17

Example 6

Preparation of a linear aminopolyether using substoichiometric quantities of secondary amine 1000 g of the isocyanate prepolymer from Example 3 (isocyanate content 3.6%, 856 mmol NCO) are added at 100° C. to a mixture of 100 g of water, 12.9 g of dibutylamine (100 mmol) and 48 g of KOH (856 mmol) at a constant rate of 120 g of isocyanate prepolymer per hour. Stirring is continued at this temperature for 2 hours after termination of the reaction, and the volatile constituents are then distilled off at 15 Torr. The oily residue is taken up with 800 ml of dichloromethane, freed from carbonic acid salt by suction filtration and again freed from solvent at 80° C./18 mbar and then at 100° C./1.33 mbar.

Product data:
Yield (%): 86
NH number (mg KOH/g): 47.4
Acid number (mg KOH/g): 0.05
Molecular weight: 2400
Viscosity (mPa.s) (at 75° C.): 435
Water content (%) (Karl Fischer): 0.06

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of aromatic polyamines comprising hydrolyzing a urea in the presence of a base, characterized in that the urea corresponds to the general formula:

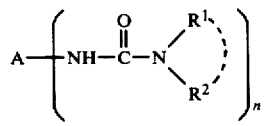

wherein
A denotes a residue obtained by the removal of n isocyanate groups from an isocyanate compound which contains urethane, urea, allophanate, biuret, isocyanurate, and/or ether groups and has the isocyanate groups directly attached to aromatic residues,
$R^1$ and $R^2$ denote, independently of each other, a linear, branched or cyclic, saturated hydrocarbon group containing 1 to 10 carbon atoms, or together form a ring having 4 to 6 ring carbon atoms, and n denotes an integer of from 2 to 4.

2. A process according to claim 1, characterized in that the alkaline hydrolysis is carried out using aqueous alkali metal hydroxides.

3. A process according to claim 1, characterized in that $R^1$ and $R^2$ denote, independently of each other, methyl, ethyl, n-propyl, i-propyl, n-butyl, i-butyl or secondary butyl.

4. A process according to claim 1, characterized in that the compound corresponding to the general formula:

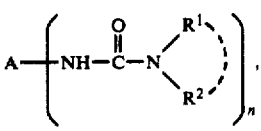

constitutes a reaction product of a secondary amine corresponding to the general formula:

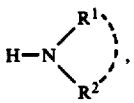

wherein $R^1$ and $R^2$ are as defined in claim 1,
and an isocyanate compound corresponding to the general formula:

wherein A and n have the meanings defined in claim 1.

5. A process according to claim 4, characterized in that said isocyanate compound is a reaction product of a polyether with a molecular weight of from 400 to 6,000 containing 2 to 4 hydroxyl groups and an aromatic polyisocyanate, using an NCO:OH ratio of from 1.5:1 to 2.8:1.

6. A process according to claim 5, characterized in that said isocyanate compound is a reaction product of said polyether and a polyol with a molecular weight of from 62 to 399 and an aromatic polyisocyanate.

7. A process for the preparation of aromatic polyamines characterized in that an isocyanate compound corresponding to the general formula:

wherein
A denotes a residue obtained by the removal of n-isocyanate groups from a compound containing urethane, urea, biuret, allophanate, isocyanurate, and/or ether groups and having aromatically-bound isocyanate groups, and
n denotes an integer from 2 to 4,
is treated, at from 0° to 60° C., with a mixture of
(a) water,
(b) from 0.1 to 10 equivalents (based on 1 equivalent of NCO) of a secondary amine corresponding to the general formula:

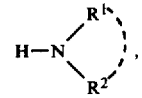

wherein $R^1$ and $R^2$ denote, independently of each other, a linear or branched aliphatic or cycloaliphatic, saturated hydrocarbon group containing from 1 to 10 carbon atoms or together denote a heterocyclic ring containing 4 to 6 ring carbon atoms,
(c) from 0 to 2 equivalents of a base containing OH⊖ groups (based on 1 equivalent of NCO), (d) from 0 to 2 equivalents of a compound containing t-amino groups (based on 1 equivalent of NCO) and (e) from 0 to 100 parts of a solvent (based on 1 part of said isocyanate compound), at least one of the components (c) and (d) being used in a quantity of from 0.1 to 2 equivalents, and the resulting aromatic polyamine is isolated from the reaction product.

8. A process according to claim 7, characterized in that component (c) consists of 1.0 to 1.5 equivalents of an alkali metal hydroxide (based on 1 equivalent of NCO).

9. A process according to claim 7, characterized in that component (d) contains 1.0 to 1.5 equivalents of tertiary amino groups to 1 equivalent of NCO.

10. A process for the preparation of compounds containing urethane and ether groups, characterized in that a urea compound prepared from dimethylamine or diethylamine and an isocyanate prepolymer which has been obtained by the reaction of a polyether with a molecular weight of from 400 to 6,000 containing 2 or 3 hydroxyl groups and an aromatic polyisocyanate, using an NCO:OH ratio in the range of 1.5:1 to 2.8:1 is treated in water at a temperature of from 40° to 100° C., with a quantity of an alkali metal hydroxide which is at least equivalent to or slightly in excess of the quantity of urea groups, and the amine end product is removed from the reaction mixture.

11. A process according to claim 10, characterized in that said isocyanate prepolymer is obtained by the reaction of a polyether and a polyol with a molecular weight of from 62 to 400 and an aromatic polyisocyanate.

* * * * *